US010726946B2

(12) United States Patent
Wang et al.

(10) Patent No.: US 10,726,946 B2
(45) Date of Patent: Jul. 28, 2020

(54) METHODS AND SYSTEMS FOR CALCULATING FREE ENERGY DIFFERENCES USING AN ALCHEMICAL RESTRAINT POTENTIAL

(71) Applicant: Schrödinger, Inc., New York, NY (US)

(72) Inventors: Lingle Wang, New York, NY (US); Yuqing Deng, New York, NY (US); Yujie Wu, New York, NY (US); Byungchan Kim, West New York, NJ (US); Robert L. Abel, Brooklyn, NY (US)

(73) Assignee: Schrödinger, Inc., New York, NY (US)

(*) Notice: Subject to any disclaimer, the term of this patent is extended or adjusted under 35 U.S.C. 154(b) by 240 days.

(21) Appl. No.: 15/683,678

(22) Filed: Aug. 22, 2017

(65) Prior Publication Data

US 2019/0065697 A1 Feb. 28, 2019

(51) Int. Cl.
*G01N 33/48* (2006.01)
*G01N 33/50* (2006.01)
(Continued)

(52) U.S. Cl.
CPC ............. *G16C 20/50* (2019.02); *G16B 15/00* (2019.02); *G16B 15/30* (2019.02); *G16C 10/00* (2019.02)

(58) Field of Classification Search
None
See application file for complete search history.

(56) References Cited

U.S. PATENT DOCUMENTS

2003/0055574 A1  3/2003  Still et al.
2007/0118296 A1* 5/2007  SantaLucia ............ G16B 15/00
                                                702/20
(Continued)

FOREIGN PATENT DOCUMENTS

EP        2509015       10/2012
JP        2012190423    10/2012

OTHER PUBLICATIONS

"Drug Design"; https://en.wikipedia.org/wiki/Drug_design; retrieved on Jul. 17, 2016; 9 pp.
(Continued)

*Primary Examiner* — Russell S Negin
(74) *Attorney, Agent, or Firm* — Fish & Richardson P.C.

(57) ABSTRACT

A method for computing free energy difference between a reference molecule and a target molecule. The target molecule has the common set of atoms $P_{AB}$ and a set of atoms $P_B$. The method includes applying a potential to restrain an interaction of the additional atomic component from the set of atoms $P_B$ with the common set of atoms $P_{AB}$ in the initial state. The method includes determining one or more transition states along a transformation path between the initial state and target state. The method includes scaling the restrain potential correspondingly along the transformation path until the potential becomes zero when a corresponding end state is reached, and calculating the free energy difference between the reference molecule and the target molecule using a value obtained along the transformation path from the initial state to the target state.

15 Claims, 8 Drawing Sheets

(51) Int. Cl.
    *G16C 20/50*     (2019.01)
    *G16B 15/00*     (2019.01)
    *G16B 15/30*     (2019.01)
    *G16C 10/00*     (2019.01)

(56) References Cited

U.S. PATENT DOCUMENTS

| | | | |
|---|---|---|---|
| 2015/0178442 | A1 | 6/2015 | Abel |
| 2015/0317459 | A1 | 11/2015 | Farhi et al. |
| 2017/0220717 | A1 | 8/2017 | Matubayasi et al. |

OTHER PUBLICATIONS

Golebiowski et al.; "Synthesis of Quaternary a-Amino Acid-based Arginase Inhibitors via the Ugi Reaction"; Bioorganic & Medicinal Chemistry Letters 23 (2013) 4837-4841.
Wang et al., "Accurate and Reliable Prediction of Relative Ligand Binding Potency in Prospective Drug Discovery by Way of a Modem Free-Energy Calculation Protocol and Force Field", J. Am. Chem. Soc. 2015, 137, 2695-2703 at 2695-6.
Moroney; Drug Action; http://www.merckmanuals.com/home/drugs/drug-dynamics/drug-action; Merck Manual; retrieved on Jul. 14, 2016.
Richardson et al., "Benzopyrans as selective estrogen receptor β agonists (SERBAs). Part 3; Synthesis of cyclopentanone and cyclohexanone intermediates for C-ring modification", Bioorganic & Medicinal Chemistry Letters 17 (2007) 4824-4828.
Boresh et al., 1998, "The Role of Bonded Terms in Free Energy Simulations: 1. Theoretical Analysis", The Journal of Physical Chemistry, 103(1):103-118.
Kollman, 1993, "Free Energy Calculations: Applications to Chemical and Biochemical Phenomena", Chemical Reviews, American Chemical Society, 93(7):2395-2417.
Smith, 1997, "A Conformational Study of 2-0xanol: Insight into the Role of Ring Distortion on Enzyme-Catalyzed Glycosidic Bond Cleavage", Journal of the American Chemical Society. 119(11):2699-2706.
Liu et al., 1996, "Estimating the Relative Free Energy of Different Molecular States with Respect to a Single Reference State", The Journal of Physical Chemistry, 100(22):9485-9494.
Beroza et al. Protonation of +A11:A21interacting residues in a protein by a Monte Carlo method: Application to lysozyme and the photosynthetic reaction center of Rhodobacter sphaeroides. PNAS, 1991, vol. 88, pp. 5804-5808.
Tester et al. Thermodynamics and Its Applications, 3rd edition. Upper Saddle River, New Jersey: Prentice Hall PTR, 1997, pp. 441-447.
Brooks et al. CHARMM: A program for macromolecular energy, minimization, and dynamics calculation. Journal of Computational Chemistry, 1983, vol. 4, pp. 187-217.
Quinone, 2005, 2 pages. The crystal reference encyclopedia. Obtained online on Jun. 30, 2014 from <<http://www.credoreference.com>>.
Li et al. Forging the missing link in free energy estimations—lambda—WHAM in thermodynamic integration, overlap histogramming, and free energy perturbation. Chemical Physics Letters, vol. 440, 2007, pp. 155-159.

Garate et al., "Free-Energy Differences between States with Different Conformational Ensembles," Journal of Computational Chemistry, vol. 34, dated Jun. 5, 2013, 11 pages.
Riniker et al., "Calculation of Relative Free Energies for Ligand-Protein Binding, Solvation, and Conformational Transitions Using the GROMOS Software," Journal of Physical Chemistry B, vol. 115 No. 46, dated Nov. 24, 2011, 8 pages.
Wikipedia.org' [online]. "Statistical ensemble," Nov. 16, 2017, [retrieved on Feb. 19, 2017]. Retrieved from the Internet: URL<https://en.wikipedia.org/wiki/Statistical_ensemble_ (mathematical_physics)> 9 pages.
Wikipedia.org' [online]. "Canonical ensemble," Jan. 11, 2018, [retrieved on Feb. 19, 2017]. Retrieved from the Internet: URL<https://en.wikipedia.org/wiki/Canonical_ensemble> 8 pages.
Wikipedia.org' [online]. "Isothermal-isobaric ensemble," Sep. 18, 2014, [retrieved on Feb. 19, 2017]. Retrieved from the Internet: URL< https://en.wikipedia.org/wiki/Isothermal%E2%80%93isobaric_ensemble> 1 page.
Wikipedia.org' [online]. "Grand canonical ensemble," Dec. 24, 2017, [retrieved on Feb. 19, 2017]. Retrieved from the Internet: URL<https://en.wikipedia.org/wiki/Grand_canonical_ensemble> 11 pages.
Wikipedia.org' [online]. "Microcanonical ensemble," Sep. 13, 2017, [retrieved on Feb. 19, 2017]. Retrieved from the Internet: URL< https://en.wikipedia.org/wiki/Microcanonical_ensemble> 7 pages.
Wikipedia.org' [online]. "Bennett acceptance ratio," Aug. 17, 2017, [retrieved on Feb. 19, 2017]. Retrieved from the Internet: URL<https://en.wikipedia.org/wiki/Bennett_acceptance_ratio> 5 pages.
Wikipedia.org' [online]. "Thermodynamic integration," Sep. 18, 2017, [retrieved on Feb. 19, 2017]. Retrieved from the Internet: URL<https://en.wikipedia.org/wiki/Thermodynamic_integration> 1 page.
Wikipedia.org' [online]. "Interval (mathematics)," Dec. 19, 2017, [retrieved on Feb. 19, 2017]. Retrieved from the Internet: URL<https://en.wikipedia.org/wiki/Interval_(mathematics)> 7 pages.
Wang et al., "Absolute Binding Free Energy Calculations Using Molecular Dynamics Simulations with Restraining Potentials," Biophysical Journal, dated Oct. 2006, 17 pages.
Mobley et al., "Perspective-Alchemical free energy calculations for drug discovery", J. 1-22 Chem. Phys., dated Dec. 21, 2012, 12 pages.
AlchemistryWiki' [online]. "Weighted histogram analysis method," Jul. 17, 2013, [retrieved on Feb. 19, 2017]. Retrieved from the Internet: URL<http://www.alchemistry.org/wiki/Weighted_Histogram_Analysis_Method> 3 pages.
PCT International Search Report and Written Opinion from PCT/US2013/077372 dated Jul. 7, 2014, 11 pages.
Response to Rule 161(1) and 162 EPC Communication dated Aug. 31, 2016 in European Application No. 13829025.9, dated Mar. 8, 2017, 13 pages (with English translation).
International Preliminary Report on Patentablity in International Application No. PCT/US2013/077372, dated Jun. 28, 2016, 9 pages (with English translation).
PCT International Search Report in International Application No. PCT/US 18/47238, dated Nov. 9, 2018, 3 pages.
International Preliminary Report on Patentability in International Application No. PCT/US2018/047238, dated Feb. 25, 2020, 7 pages.

\* cited by examiner

METHODS AND SYSTEMS FOR CALCULATING FREE ENERGY DIFFERENCES USING AN ALCHEMICAL RESTRAINT POTENTIAL

BACKGROUND

Free energy is a fundamental molecular property that plays an important role in characterizing chemical and biological systems. An understanding of the free energy behavior of many chemical and biochemical processes, such as protein-ligand binding, can be of importance in endeavors such as rational drug design (which involves the design of small molecules that bind to a biomolecular target).

Computer modeling and simulations are often used in free energy studies. In most instances, evaluation of accurate absolute free energies from simulations is extremely difficult, if at all possible. Hence, the free energy difference between two well-delineated thermodynamic states, or relative free energy, are often used as a study system to provide insight to particular systems, such as a relative binding affinity of a ligand predicated on the measured affinity of a different but similar ligand (e.g., a congeneric ligand).

In the relative free energy calculations, the two thermodynamic states can be referred to as a reference molecule and a target molecule, which can represent respectively an initial state of a molecular system, such as a first molecule, and an ending state of the molecule after one or more transformations have taken place (such as a conformational change, topological change, or a replacement of one atom or chemical group with another (i.e., a mutation)). The term "molecule" can refer to both neutral and charged species. Such transformations may not always represent realistic physical transformations, but may involve nonphysical or "alchemical" transformations. Different frameworks have been developed for calculating free energy differences, such as free energy perturbations (FEP), thermodynamic integrations (TI), and umbrella sampling.

Within the FEP framework, the free energy difference $\Delta F_{a \to b}$ between the two molecules a and b can be expressed by:

$$\Delta F_{a \to b} = -\frac{1}{\beta} \ln \langle \exp\{-\beta[\mathcal{H}_b(x, p_x) - \mathcal{H}_a(x, p_x)]\} \rangle_a \quad (1)$$

where $\beta^{-1} = k_B T$, whereis $k_B$ is the Boltzmann constant, T is the temperature. $\mathcal{H}_a(x,p_x)$ and $\mathcal{H}_b(x,p_x)$ are the Hamiltonians characteristic of states a and b respectively. $\langle (\ldots) \rangle_a$ denotes an ensemble average over configurations representative of the initial, reference molecule, a.

In practical applications of FEP, the transformation between the two thermodynamic states is usually achieved by a series of transformations between non-physical, transition states along a well-delineated pathway that connects a to b. This pathway is often characterized by a general extent parameter, often referred to as a coupling parameter, $\lambda$, which varies from 0 to 1 from the reference molecule to the target molecule, and relates the Hamiltonians of the two states by:

$$\mathcal{H}(\lambda) = (1-\lambda)H_a + \lambda H_b \quad (2)$$

where $H(\lambda)$ is the $\lambda$-coupled or hybrid Hamiltonian of the system between the two states (including the two states, when $\lambda$ takes the end values of 0 and 1). Hence, the free energy difference $\Delta F_{a \to b}$ between a and b will be:

$$\Delta F_{a \to b} = -\frac{1}{\beta} \ln \langle \exp\{-\beta[\mathcal{H}(\lambda=1) - \mathcal{H}(\lambda=0)]\} \rangle_{\lambda=0} \quad (3)$$

$$= -\frac{1}{\beta} \sum_{i=0}^{N-1} \ln \langle \exp\{-\beta[\mathcal{H}(x, p_x; \lambda_{i+1}) - \mathcal{H}(x, p_x; \lambda_i)]\} \rangle_i$$

where N stands for the number of "windows" between neighboring states between the reference (initial) state and the target (final) state, and $\lambda_i$ is the values of the coupling parameter in the initial, intermediate, and final state.

The free energy difference between the reference system state a and the target system state b can also be calculated using thermodynamic integration method, where the free energy difference is calculated using the following formula:

$$\Delta F_{a \to b} = \int_{\lambda=0}^{\lambda=1} d\lambda \left\langle \frac{\partial \mathcal{H}(\lambda)}{\partial \lambda} \right\rangle_\lambda \quad (4)$$

where $\lambda$ is the coupling parameter which varies from 0 to 1 from the reference state to the target molecule, H($\lambda$) is the $\lambda$-coupled or hybrid Hamiltonian of the system between the two states (including the two states, when $\lambda$ takes the end values of 0 and 1), and $$\frac{\partial \mathcal{H}(\lambda)}{\partial \lambda}$$

is the first derivative of the coupled Hamiltonian with respect to the coupling parameter $\lambda$. In practical applications of TI, the transformation between the reference system state and the target system state is achieved by a series transformations along a well-delineated pathway that connects a to b, and the ensemble average of $$\frac{\partial \mathcal{H}(\lambda)}{\partial \lambda}$$

is calculated for all the states sampled, including the reference system state, the intermediate non-physical states, and the target system state. The free energy difference between the reference system state and the target system state is then approximated by numerical integration of the above integral based on the value of the $$\left\langle \frac{\partial \mathcal{H}(\lambda)}{\partial \lambda} \right\rangle_{\lambda_i},$$

where $\lambda_i$ is the values of the coupling parameter in the initial, intermediate, and final states.

SUMMARY

In drug lead optimizations, a lead compound that binds a desired target is known and derivatives of this lead compound are created that either improve the affinity or maintain the affinity while improving other properties. Relative binding free energy (RBFE) calculations based on molecular dynamics (MD) simulations, for example, can be used to predict binding free energy differences based on chemical changes in advance of synthesis of the derivative compounds. Such calculations allow researchers to screen derivative compounds computationally, before investing in the compounds synthesis and lab testing. Thus, they can potentially substantially accelerate the lead optimization process and are of considerable interest for drug discovery applications.

In alchemical free energy calculations to transform from molecule A in an initial state (e.g., the drug lead compound) to molecule B in a target molecule (e.g., derivatives of the lead compound), when each of molecules A and B has different number of atoms and different chemistries, there are two desired conditions:

1. The first condition is that interactions between any additional atoms in molecule B and a common part of the two molecules should not introduce artificial couplings to physical atoms in molecule A in the initial state. Similarly, the interactions between any additional atoms in molecule A and the common part of the two molecules should also not introduce artificial couplings to the physical atoms in molecule B in the final state.
2. The second condition is that interactions between the common part of the molecules and a mutated part of the molecules be set such that a configurational space overlap between the two molecules is maximized. Maximizing the configurational space overlap can reduce the sampling time needed to get converged free energy calculations.

The methods described in this application can allow both conditions to be balanced to achieve accurate and reliable free energy calculations, improving upon prior methods that fail to satisfy both conditions simultaneously. In one aspect, a method for computing a free energy difference between a reference molecule and a target molecule, the method includes providing relative spatial arrangements of atoms and bonded connections between atoms in i) the reference molecule, the reference molecule comprising a common set of atoms $P_{AB}$ and a set of atoms $P_A$, and ii) the target molecule, the target molecule comprising the common set of atoms $P_{AB}$ and a set of atoms $P_B$. The method includes defining an initial state, the initial state being a non-physical molecule composed of the reference molecule and at least one additional atomic component from the set of atoms $P_B$. The method includes defining a target state, the target state being a non-physical molecule composed of the target molecule and at least one additional atomic component from the set of atoms $P_A$. The method includes applying a potential to restrain an interaction of the additional atomic component from the set of atoms $P_B$ with the common set of atoms $P_{AB}$ in the initial state; applying a potential to restrain an interaction of the additional atomic component from the set of atoms $P_A$ with the common set of atoms $P_{AB}$ in the target state. The method includes determining one or more transition states along a transformation path between the initial state and target state. The method includes scaling the restrain potential correspondingly along the transformation path until the potential becomes zero when a corresponding end state is reached. The method includes turning on remaining bonded interactions between the at least one additional atomic component in $P_B$ with the common set of atoms $P_{AB}$ and non-bonded interactions along the transformation path until the target state is reached. The method includes turning on remaining bonded interactions between the at least one additional atomic component in $P_A$ with the common set of atoms $P_{AB}$ and the non-bonded interactions along a reverse direction of the transformation path until the initial state is reached. The method includes calculating the free energy difference between the reference molecule and the target molecule using a value obtained along the transformation path from the initial state to the target state. Applying the potential increases the accuracy of the free energy difference calculated while maintaining a configurational space overlap of the initial state and the target state.

Implementations can include one or more of the following features. The value can include an energy difference, a derivative of the energy difference, or quantities related to the energy difference. The at least one additional atomic component from the set of atoms $P_B$ in the initial state can include the set of atoms $P_B$ and the at least one additional atomic component from the set of atoms $P_A$ in the target state includes the set of atoms $P_A$. The additional atomic component from the set of atoms $P_B$ can be bonded to an atom in $P_{AB}$ in the target molecule, the potential can be a harmonic potential for a dihedral angle defined by a plane containing three atoms in $P_{AB}$ and a plane containing two atoms in $P_{AB}$ and the additional atomic component from the set of atoms $P_B$. The atom in $P_{AB}$ can be bonded to the atom in $P_B$ in the target molecule is in a sp2 hybridization, and an equilibrium angle of the potential can be set at 180°. Determining the one or more transition states along the transformation path can include calculating a bond stretch interaction between the atom in $P_{AB}$ and the additional atomic component from the set of atoms $P_B$, and one bond angle interaction. The additional atomic component from the set of atoms $P_A$ can be bonded to an atom in $P_{AB}$ in the reference molecule, the potential can be a harmonic potential for a dihedral angle defined by a plane containing three atoms in $P_{AB}$ and a plane containing two atoms in $P_{AB}$ and the additional atomic component from the set of atoms $P_A$. The atom in $P_{AB}$ bonded to the atom in $P_A$ in the initial molecule can be in a sp2 hybridization, and an equilibrium angle of the potential is set at 180°. Determining the one or more transition states along the transformation path can include calculating a bond stretch interaction between the atom in $P_{AB}$ and the additional atomic component from the set of atoms $P_A$, and one bond angle interaction. Applying a potential to restrain an interaction of the additional atomic component from the set of atoms $P_B$ can include restraining a set of interactions of the additional atomic component from the set of atoms $P_B$ with the common set of atoms $P_{AB}$ in the initial state. Applying a potential to restrain an interaction of the additional atomic component from the set of atoms PA can include restraining a set of interactions of the additional atomic component from the set of atoms $P_A$ with the common set of atoms $P_{AB}$ in the target state. Applying the potential and using only one bond angle interaction can increase an accuracy of the free energy difference calculation while preventing the additional atomic component from the set of atoms $P_B$ or $P_A$ from orienting in nonphysical geometry. The atom in $P_{AB}$ can be bonded to the additional atomic component from the set of atoms $P_B$ in the target molecule can be in a sp3 hybridization, and an equilibrium angle of the potential can be set at 120°. The atom in $P_{AB}$ bonded to the additional atomic component from the set of atoms $P_A$ in the initial molecule can be in a sp3 hybridization, and an equilibrium angle of the potential can be set at 120°.

An interaction of the at least one additional atomic component from the set of atoms $P_B$ in the target molecule and the atoms in $P_{AB}$ can be the same when the reference molecule is in a complex form and when the reference molecule is in a solvent. An interaction of the at least one additional atomic component from the set of atoms $P_A$ in the initial molecule and the atoms in $P_{AB}$ can be the same when the target state is in a complex form and when the target state in in a solvent.

In another aspect, a nontransitory computer readable medium, storing the instructions which when executed by one or more processors, carry out the method of computing free energy difference between a reference molecule and a target molecule, the method includes providing relative spatial arrangements of atoms and bonded connections between atoms in i) the reference molecule, the reference molecule comprising a common set of atoms $P_{AB}$ and a set of atoms $P_A$, and ii) the target molecule, the target molecule comprising the common set of atoms $P_{AB}$ and a set of atoms $P_B$. The method includes defining an initial state, the initial state being a non-physical molecule composed of the reference molecule and at least one additional atomic component from the set of atoms $P_B$. The method includes defining a target state, the target state being a non-physical molecule composed of the target molecule and at least one additional atomic component from the set of atoms $P_A$. The method includes applying a potential to restrain an interaction of the additional atomic component from the set of atoms $P_B$ with the common set of atoms $P_{AB}$ in the initial state; applying a potential to restrain an interaction of the additional atomic component from the set of atoms $P_A$ with the common set of atoms $P_{AB}$ in the target state. The method includes determining one or more transition states along a transformation path between the initial state and target state. The method includes scaling the restrain potential correspondingly along the transformation path until the potential becomes zero when a corresponding end state is reached. The method includes turning on remaining bonded interactions between the at least one additional atomic component in $P_B$ with the common set of atoms $P_{AB}$ and non-bonded interactions along the transformation path until the target state is reached. The method includes turning on remaining bonded interactions between the at least one additional atomic component in $P_A$ with the common set of atoms $P_{AB}$ and the non-bonded interactions along a reverse direction of the transformation path until the initial state is reached. The method includes calculating the free energy difference between the reference molecule and the target molecule using a value obtained along the transformation path from the initial state to the target state. Applying the potential increases the accuracy of the free energy difference calculated while maintaining a configurational space overlap of the initial state and the target state.

Implementations can include one or more of the following features. The at least one additional atomic component from the set of atoms $P_B$ in the initial state can include the set of atoms $P_B$ and the at least one additional atomic component from the set of atoms $P_A$ in the target state can include the set of atoms $P_A$. The atom in $P_B$ can be bonded to an atom in $P_{AB}$ in the target molecule, the potential is a harmonic potential for a dihedral angle defined by a plane containing three atoms in $P_{AB}$ and a plane containing two atoms in $P_{AB}$ and the atom in $P_B$. The atom in $P_{AB}$ can be bonded to the atom in $P_B$ in the target molecule is in a sp2 hybridization, and an equilibrium angle of the potential can be set at 180°. Determining the one or more transition states along the transformation path can include calculating a bond stretch interaction between the atom in $P_{AB}$ and the atom in $P_B$, and one bond angle interaction. Applying the potential and using only one bond angle interaction can increase an accuracy of the free energy difference calculation while preventing the additional atomic component from the set of atoms $P_B$ from orienting in nonphysical geometry. The atom in $P_{AB}$ can be bonded to the additional atomic component from the set of atoms $P_B$ in the target molecule can be in a sp3 hybridization, and an equilibrium angle of the potential can be set at 120°. An interaction of the at least one additional atomic component from the set of atoms $P_B$ in the initial state and the atoms in $P_{AB}$ can be the same when the reference molecule is in a complex form and when the reference molecule in in a solvent. An interaction of the at least one additional atomic component from the set of atoms $P_B$ in the target state and the atoms in $P_{AB}$ can be the same when the target state is in a complex form and when the target state is in a solvent.

The invention also provides an apparatus including one or more processors, a memory operably coupled to the one or more processors having instructions executable by the processors, the one or more processors being operable when executing the instructions to perform the various embodiments of the method as described herein. The invention further provides non-transitory computer readable media storing the instructions which when executed by one or more processors, carry out the various embodiments of the method as described herein.

Other features and advantages of the invention are apparent from the following description, and from the claims.

DETAILED DESCRIPTION

The present application discloses computer-implemented methods and systems for computing a free energy difference between a reference molecule and a target molecule that 1) reduce artificial couplings between physical atoms in a molecule in the reference system state (or the target molecule) and the additional atoms in a molecule in the target molecule (of the reference molecule), and 2) maximizes the configurational space overlap between the two molecules. The methods and systems disclosed in the present application utilize an alchemical restraint potential in the alchemical transformation for calculating the free energy difference. Accordingly, the methods and systems of the present application can advantageously improve efficiency and accuracy of the free energy calculations. The general principles of the free energy calculations using such alchemical restraint potentials disclosed can be applied generally in any functional group mutation transformations, atom mutation transformations or bond formation and breaking transformations, and not limited to mutation described in this document.

Figure 1:
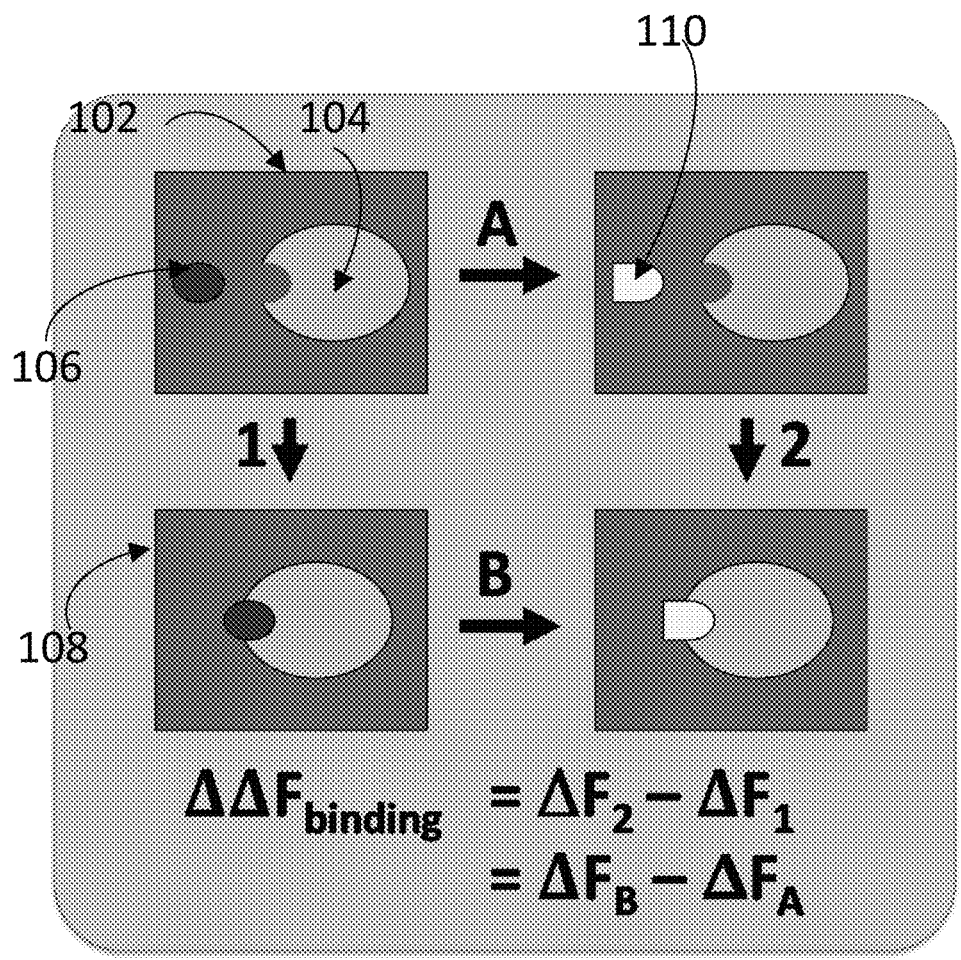
FIG. 1 is a schematic of a thermodynamic cycle.

FIG. 1 shows a thermodynamic cycle for a system 102 which has a receptor 104 in solution in a solvent (e.g., water) and a ligand 106 also in solution. When the ligand 106 binds with the receptor 104 as shown by an arrow denoted by "1", a complex system 108 is formed. The free energy associated with the binding of the ligand 106 with the receptor 104 (i.e., taking the ligand from the solvent/water to the "binding site") is denoted by $\Delta F_1$. When a different ligand 110 is used, the free energy of binding of the ligand 110 with the receptor 104 is denoted by $\Delta F_2$. The relative binding free energy $\Delta\Delta F_{binding}$ is obtained by taking the difference between the two free energy of binding. This relative binding free energy can also be obtained by calculating the free energy change by alchemically transforming ligand 106 ("molecule 1") into ligand 110 ("molecule 2") both in solvent (e.g., water), $\Delta F_A$, and also in the binding site, $\Delta F_B$.

As with traditional free energy difference calculations, the atoms in the system can be categorized into different groups for evaluating the system energy in different molecules. The reference molecule and target molecule both include a common set of atoms $P_{AB}$. The reference molecule further includes a set of atoms $P_A$, and the target molecule further includes a set of atoms $P_B$. The set of atoms $P_A$ are present only in the reference molecule and not in the target molecule, and the set of atoms $P_B$ are present only in the target molecule and not the reference molecule. During the course of the transformation, the atoms in $P_A$ and in $P_B$ interact with other atoms within their own set as well as with those in $P_{AB}$, but the atoms in $P_A$ do not interact with any atoms in $P_B$, or vice versa.

To simplify the energy difference calculation, dummy atoms are introduced in the free energy perturbation (FEP) to preserve the number of atoms between the two end states (i.e., the reference molecule and the target molecule). Dummy atoms are defined as atoms that no longer have charge or Lennard-Jones interactions with the remainder of the system but retain their bonded interactions. The reference molecule containing the reference molecule and the dummy atoms contained in the target molecule is labeled "initial state", and the target molecule containing the target molecule and the dummy atoms contained in the reference molecule is labeled "target state".

Figure 2:
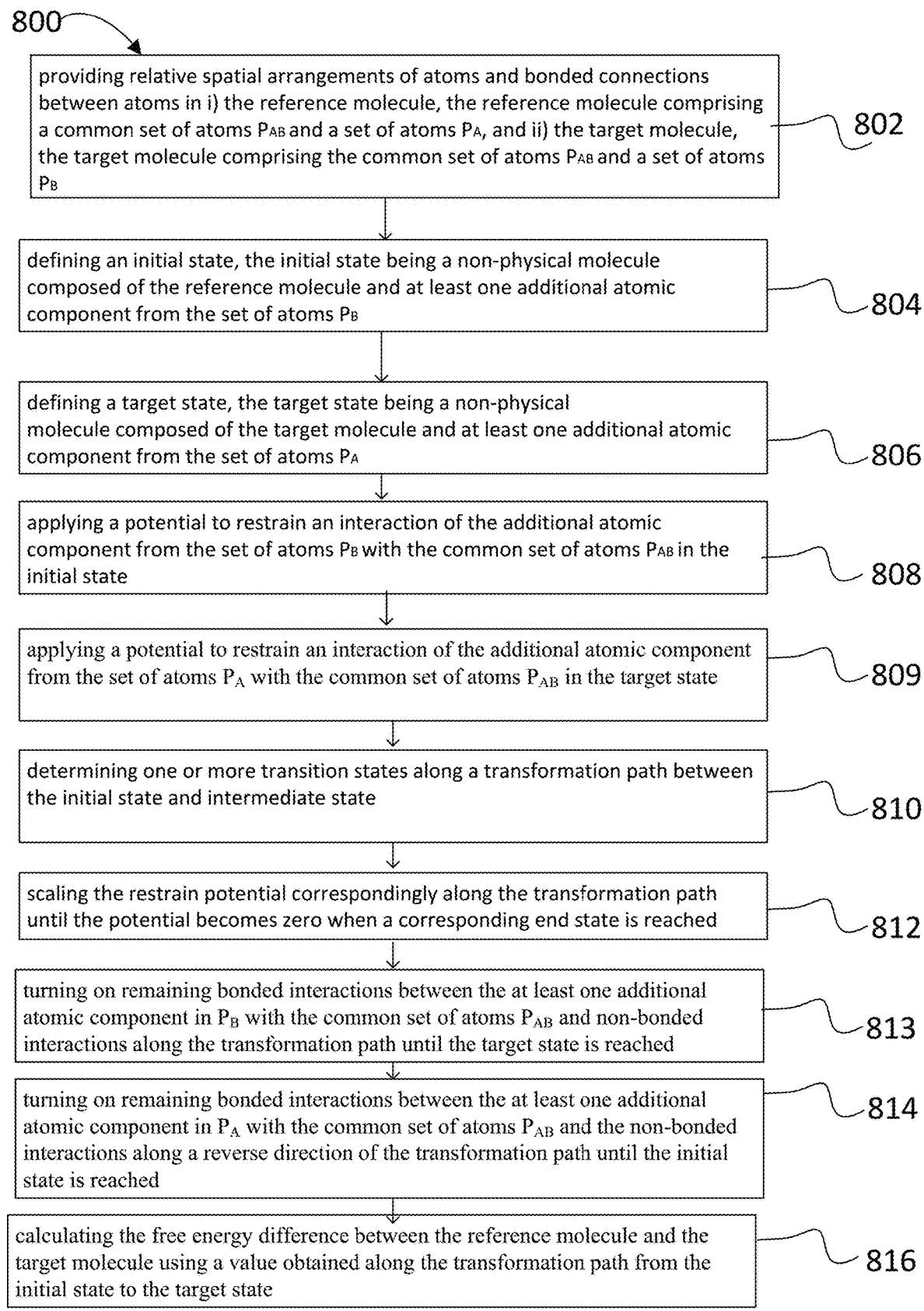
FIG. 2 is a flow chart describing the methods and systems disclosed herein.

FIG. 2 shows a flow chart of a method 800 for computing free energy difference between a reference molecule and a target molecule. At a step 802, the method involves providing relative spatial arrangements of atoms and bonded connections between atoms in i) the reference molecule, the reference molecule having a common set of atoms $P_{AB}$ and a set of atoms $P_A$, and ii) the target molecule, the target molecule having the common set of atoms $P_{AB}$ and a set of atoms $P_B$. At a step 804, the method includes defining an initial state, the initial state being a non-physical molecule composed of the reference molecule and at least one additional atomic component from the set of atoms $P_B$. At a step 806, the method includes defining a target state, the target state being a non-physical molecule composed of the target molecule and at least one additional atomic component from the set of atoms $P_A$.

At a step 808, the method includes applying a potential to restrain an interaction of the additional atomic component from the set of atoms PB with the common set of atoms PAB in the initial state.

At a step 809, the method includes applying a potential to restrain an interaction of the additional atomic component from the set of atoms $P_A$ with the common set of atoms $P_{AB}$ in the target state.

At a step 810, the method includes determining one or more transition states along a transformation path between the initial state and intermediate state. Thereafter, at a step 812, the method involves scaling the restrain potential correspondingly along the transformation path until the potential becomes zero when a corresponding end state is reached. At a step 813, turning on remaining bonded interactions between the at least one additional atomic component in $P_B$ with the common set of atoms $P_{AB}$ and non-bonded interactions along the transformation path until the target state is reached. At a step 814, the method includes turning on remaining bonded interactions between the at least one additional atomic component in $P_A$ with the common set of atoms $P_{AB}$ and the non-bonded interactions along a reverse direction of the transformation path until the initial state is reached. At a step 816, the method involves calculating the free energy difference between the reference molecule and the target molecule using a value obtained along the transformation path from the initial state to the target state, wherein applying the potential increases the accuracy of the free energy difference calculated while maintaining a configurational space overlap of the initial state and the target state.

Details about free energy calculations are disclosed, for example, in Applicants' pending application U.S. Ser. No. 14/138,186, entitled "Methods and Systems for Calculating Free Energy Differences Using a Modified Bond Stretch Potential", the content of which is incorporate herein by reference in its entirety.

Figure 3A:
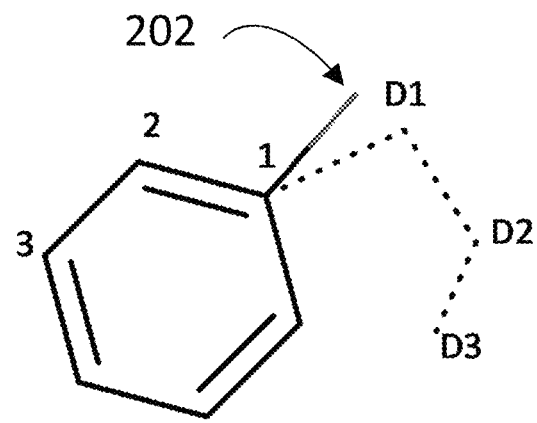
FIG. 3A is a diagram of an initial state containing a reference molecule and dummy atoms.

FIG. 3A shows the initial state containing a reference molecule and a set of 3 heavy dummy atoms, or additional atomic components. The reference molecule is a benzene molecule with an atom 202 directly bonded (i.e., covalently bonded) to carbon atom 1. A set of 3 dummy atoms D1, D2, and D3, are shown in dotted lines, with dummy atom D1 being connected to carbon atom 1 and dummy atom D2.

Figure 3B:
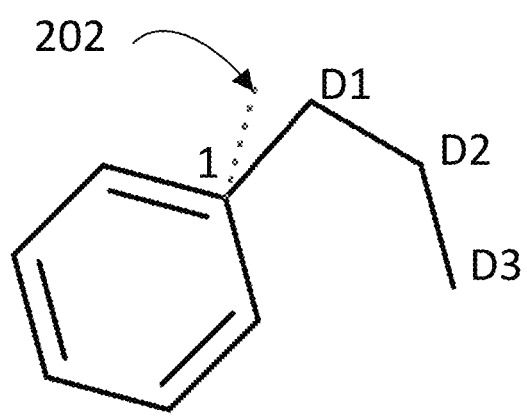
FIG. 3B is a diagram of a target state containing a target molecule and a dummy atom.

FIG. 3B shows the target state containing a target molecule and a dummy atom 202 connected to carbon atom 1 via a dotted line. The target molecule is a benzene ring having the atom D1 directly bonded (i.e., covalently bonded) to carbon atom 1. Atom D3 is also covalently bonded to atom D2, which in turn is bonded to atom D1.

To achieve physical rigor, the interactions between the dummy and the core of the molecule should satisfy the restraint:

$$\Delta F_{2c}(D_{2m}) = \Delta F_{2s}(D_{2m}) \tag{5}$$

$$\Delta F_{1c}(D_{1m}) = \Delta F_{1s}(D_{1m}) \tag{6}$$

where subscripts 1c and 2c refer to the reference molecule and the target molecule in the complex form (i.e., when the ligand is transferred from the solvent (e.g., water) to the binding site), respectively, and the subscripts 1s and 2s refer to the reference molecule and the target molecule in the solvent, respectively. $D_{1m}$ refers to the dummy atoms in the reference molecule and $D_2m$ refers to the dummy atoms in the target molecule. $\Delta F_{2c}(D_{2m})$ refers to the dummy atom contribution to the free energy of the target molecule state in the protein complex (i.e., the free energy of the target molecule state in protein complex subtracted by the free energy of the physical target molecule in the protein complex), and $\Delta F_{2s}(D_{2m})$ refers to the dummy atom contribution to the free energy for the target molecule state in the solvent (i.e., the free energy of the target molecule state in solvent subtracted by the free energy of the physical target molecule in solvent). $\Delta F_{1c}(D_{1m})$ and $\Delta F_{1s}(D_{1m})$ refer to the corresponding dummy atom contributions to the free energies of the reference molecule in complex and solvent, respectively.

Figure 4B:
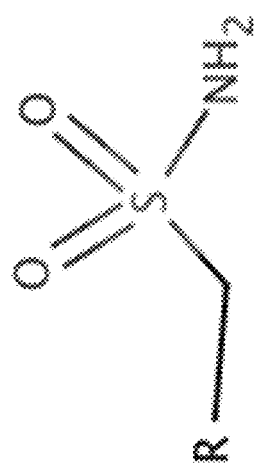
FIG. 4B is a diagram of a target molecule.
Figure 4A:
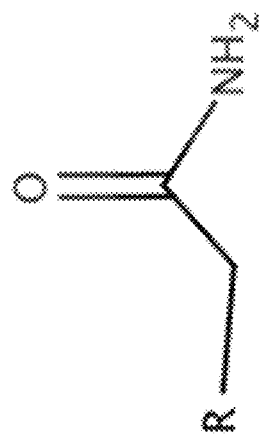
FIG. 4A is a diagram of a reference molecule.

The calculation of relative binding free energy between the reference molecule shown in FIG. 4A and the target molecule shown in FIG. 4B can be greatly improved using the methods and systems disclosed in this application. The $SO_2$ in FIG. 4A is in sp3 hybridization whereas the CO in FIG. 4B is in sp2 hybridization. One of oxygen atoms in $SO_2$ is the dummy atom in the target state, and the central S atom is directly morphed to the C atom in CO group by gradually changing its partial charge and non-bonded interactions. In this example, the equilibrium angle defined by O—C—N in the target molecule is quite different from that defined by O—S—N in the reference molecule. If two angle interactions between the dummy O atom and the rest of the molecule are retained, the wrong physical geometry for the target state corresponding to $CONH_2$ in FIG. 4B would result. As explained below, the methods and systems disclosed herein uses a single angle interaction to reduce the likelihood (i.e., prevent) the molecule in the target state from adopting the wrong physical geometry.

Figure 5B:
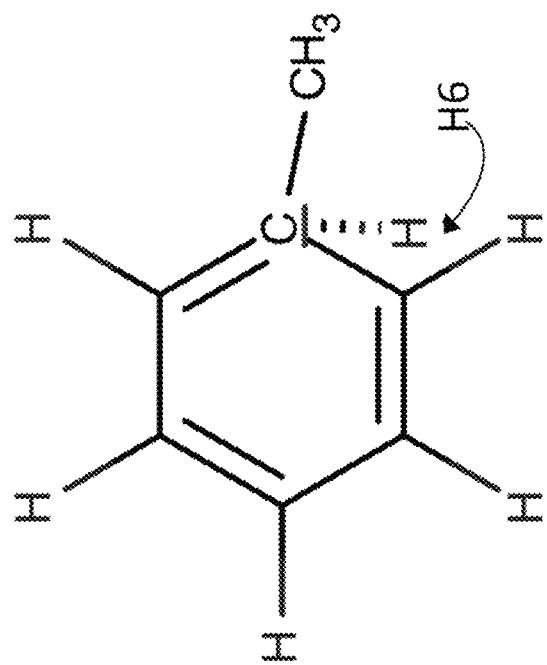
FIGS. 5A-B are different conformations of an initial state.
Figure 5A:
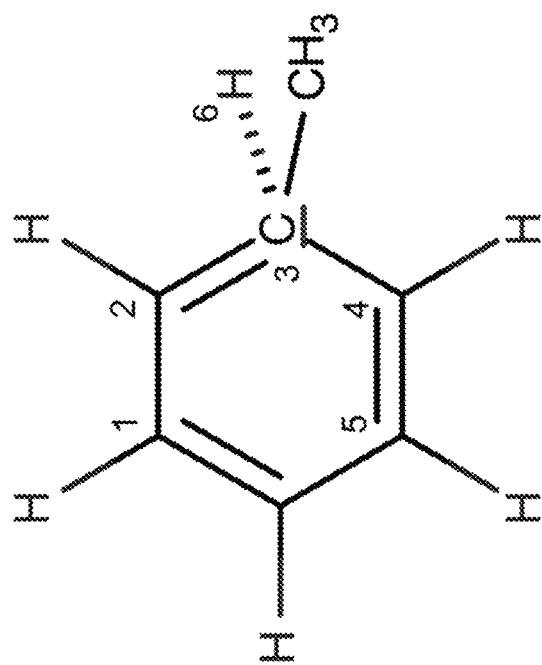

FIG. 5A shows a conformation A in which a dummy hydrogen atom 6 ("H6") is connected to carbon atom 3 in the initial state. The relative free energy calculation relates to a mutation of the $CH_3$ group bonded to carbon atom 3 into H6. To achieve physical rigor, interactions between dummy H6 and the core of the molecule should only depend on $(d_1, \theta_1, \Phi_1)$ or $(d_1, \theta_1, \Phi_2)$, but not both. $d_1$ refers to the bond stretch interaction between carbon atom 3 and the dummy H6. Alchemical transformation can generally include interactions relating to bonded stretch terms, the bonded angle terms, and the bonded dihedral angle terms.

A variety of different approaches can be used to perform the free energy calculations. Several approaches are described below as examples.

Approach 1

The first approach covers calculations that use only the combination of 1) a single bond stretch, 2) a single bond angle interaction, and 3) a single bond dihedral angle interaction. The first approach results in poor configurational space overlap because dummy H6 can flip back, as shown in FIG. 5B, each depicting conformation B and conformation C, respectively. Such orientation of H6 is not physical because the carbon 3 atom to which the dummy H6 is connected to is in sp2 hybridization, and the dummy H6 should generally not deviate from the plane defined by the benzene portion of the molecule. In other words, when H6 becomes a real physical atom in the target molecule, H6 should only point to the geometry corresponding to conformation A. Therefore, the conformational differences between conformation B for the initial molecule versus conformation A for the target molecule result in large gap in configurational space between the two end states, leading to large sampling errors in the free energy calculations. Thus, bonded dihedral angle interaction is not sufficient to prevent the dummy atoms pointing into nonphysical geometry, which results in poor configurational space overlap.

Approach 2

Figure 7:
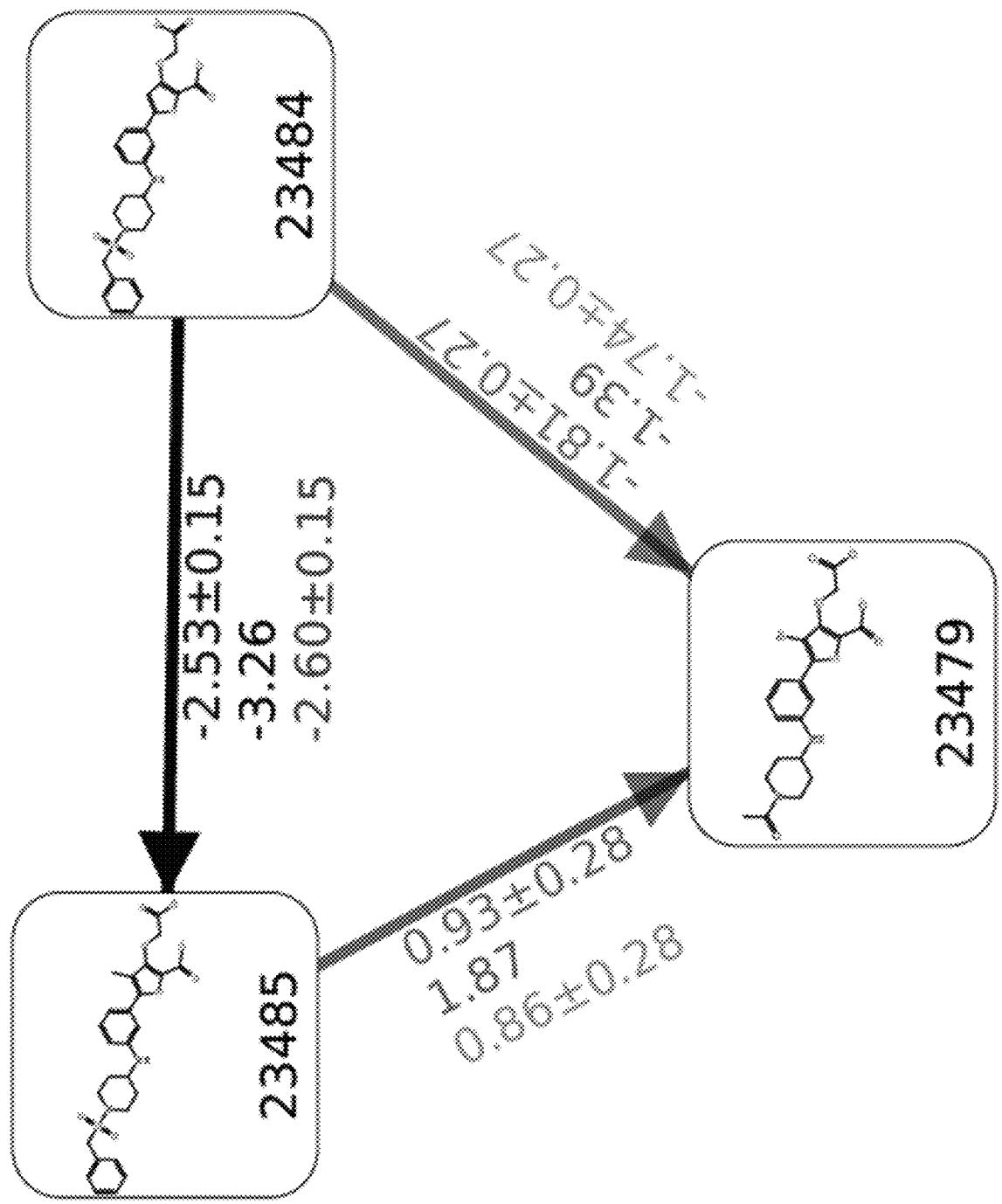
FIG. 7 is a diagram showing results obtained using one approach.

To maximize phase space overlap or configurational space overlap some calculations retain interactions involving both $\theta_1$ and $\theta_1$. Such an approach prevents the dummy H6 from pointing into nonphysical geometry, but breaks physical rigor, (i.e., does not yield accurate calculations that reflect experimental results) as the dummy H6 free energy does not exactly canceled out in complex ($\Delta F_B$) and solvent ($\Delta F_A$) simulations. An example demonstrating the errors from this approach for the mutation shown in FIG. 4 is provided in the following (FIG. 7).

Approach Using Alchemical Restraint Potential

To achieve physical rigor, interactions between dummy H and the core of the molecule should only depend on $(d_1, \theta_1, \Phi_1)$ or $(d_1, \theta_1, \Phi_2)$, or $(d_1, \theta_1/\theta_2, \omega)$ but not two or more. $\omega$ is the dihedral angle between the plane defined by atoms 2,3,4 in the benzene ring and the plane defined by atoms 2, 3, and dummy H6.

In the initial state where H6 is dummy atom, the calculation retains bond stretch interaction $d_1$, one bond angle interaction (either $\theta_1$ or $\theta_2$, but not both), and a harmonic potential for $\omega$ with equilibrium angle of 180 degrees. The harmonic potential $U(\omega)$ is a simple harmonic oscillator potential, $U(\omega) = K(\omega - \omega_0)^2$ where K is a force constant, and $\omega_0$ is the equilibration dihedral angle, which is 180 degrees in this case.

The calculation then scales the harmonic potential slowly to 0 when transforming from the initial state to the final state along a transformation path. All other bonded interactions between H6 and the core of the molecule is slowly turned on as well when H becomes real (in the target state).

The alchemical restraint potential achieves physical rigor, and maintains a good configurational space overlap between the two end points (i.e., the initial molecule and the target molecule samples approximately the same ensemble of configurations).

Figure 6A:
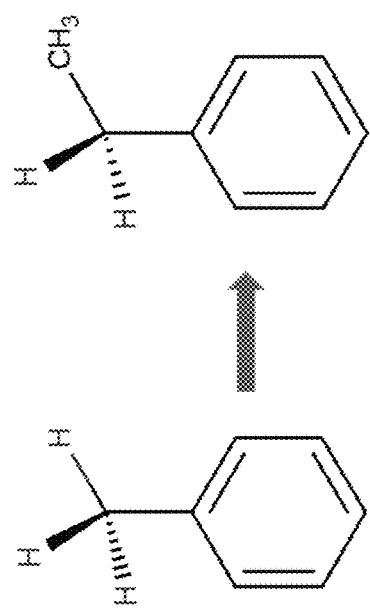
FIG. 6A is a diagram showing a mutation of a reference molecule into a target molecule.

FIG. 6A shows another example of the use of the alchemical restraint potential to achieve the twin objective of maximizing configurational space overlap and maintaining physical rigor. The reference molecule is methylbenzene, and the target molecule is ethylbenzene, in which one of the hydrogen atoms in the methyl group of the reference molecule is mutated to a methyl ($CH_3$) group.

Figure 6B:
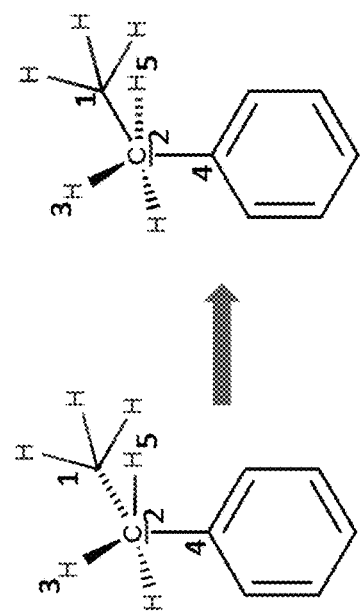
FIG. 6B is a diagram showing a transformation of an initial state into an target state corresponding to the mutation in FIG. 6A.

FIG. 6B shows the initial state that is formed using the reference molecule together with the addition of the dummy atoms (i.e., $CH_3$) found in the target molecule. The target state is formed using the target molecule together with the addition of the dummy atom (i.e., H) found in the reference molecule.

In the initial state, the calculation uses a harmonic potential on the dihedral angle between 324 plane (i.e., plane containing hydrogen atom 3, carbon atom 2, and the carbon atom 4) and 321 plane (i.e., plane containing hydrogen atom 3, carbon atom 2, and the dummy carbon atom 1). In the target state, the calculation uses a harmonic potential on the dihedral angle between 324 plane and 325 plane (i.e., plane containing hydrogen atom 3, carbon atom 2, and the dummy hydrogen atom 5). The above harmonic potentials are scaled down to 0 in the corresponding end state when the respective dummy atom(s) become physical atom(s).

FIG. 7 shows a calculation done using Approach 2. The desired free energy differences are the mutations among molecules 23484, 23485 and 23479. The calculations include, the free energy difference between molecule 23484 and molecule 23479 (involving the addition of a Br atom, the elimination of a methyl-benzene group, and the conversion of $SO_2$ into $CO_2$ group), the free energy difference between molecule 23485 and molecule 23479 (involving the replacement of a methyl group to a Br atom, the elimination of a methyl-benzene group, and the conversion of $SO_2$ into $CO_2$ group), and the free energy difference between molecule 23484 and molecule 23485 (involving the addition of a methyl group). Table 1 tabulates the results from the calculation based on Approach 2.

TABLE 1

Results obtained using Approach 2.

| | 23484 → 23479 | 23485→ 23479 | 23484→ 23485 |
|---|---|---|---|
| Experimental data | −1.39 | 1.87 | −3.26 |
| Direct simulation results | −1.81 ± 0.27 | 0.93 ± 0.28 | −2.53 ± 0.15 |
| Cycle closure corrected results | −1.74 ± 0.27 | 0.86 ± 0.28 | 2.60 ± 0.15 |

Figure 8:
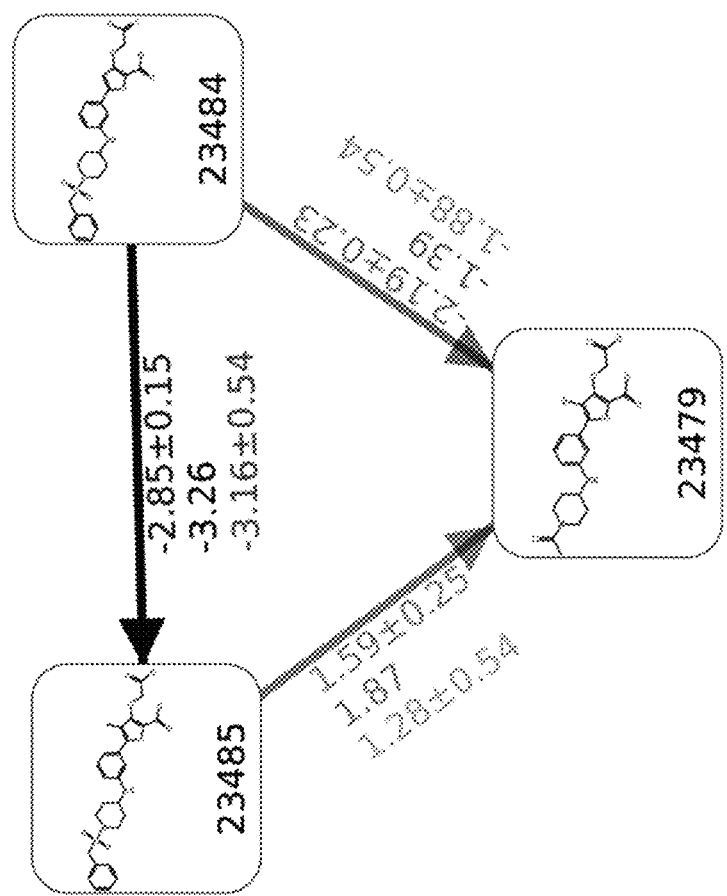
FIG. 8 is a diagram showing results obtained using the methods and systems disclosed herein.

FIG. 8 shows a calculation done using the methods and systems disclosed herein for the same system as shown in FIG. 7.

TABLE 2

Results obtained using the methods and systems disclosed herein.

| | 23484 → 23479 | 23485→ 23479 | 23484→ 23485 |
|---|---|---|---|
| Experimental data | −1.39 | 1.87 | −3.26 |
| Direct simulation results | −2.19 ± 0.23 | 1.59 ± 0.25 | −2.85 ± 0.15 |
| Cycle closure corrected results | −1.88 ± 0.54 | 1.28 ± 0.54 | −3.16 ± 0.54 |

As shown in FIG. 8 and Table 2, the results using alchemical restraints is much closer to the experimental values compared to the results obtained using Approach 2.

For a mutation involving sp hybridization, for example, mutation of a H atom that is bonded to a carbon triple bond into a $CH_3$ group that is bonded to a carbon triple bond. In such a case, the initial state would contain $CH_3$ as the dummy atoms, and the final state would contain a dummy H atom. However, as the carbon atom in $CH_3$, the carbon atom in the triple bond, and the other carbon atom in the triple bond form a linear geometry, no alchemical restraint potential needs to be used in such a case to restrain the dihedral angle as was done in the previous examples.

As an initial step, the topology of the system is provided, including the bonded connections between the atoms in the system and the relative spatial arrangements of the atoms forming each of $P_{AB}$, $P_A$, and $P_B$.

One or more, e.g., a plurality of transition states between the reference molecule and the target molecule can be determined along a path defined by different values of the coupling parameter $\lambda$, where the increments of $\lambda$ in value move the system from the reference molecule to the target molecule. While $\lambda$ can be a scalar variable that varies from 0 to 1, in some embodiments of the present invention, such as those further discussed below, $\lambda$ can be a vector containing different components for different types of interactions within the system. Computer molecular simulations, such as, but not limited to, molecular dynamics or Monte Carlo simulations, can be performed to obtain ensembles of the micro-states for the reference molecule, the target molecule, and each of the transition states. The $\lambda$ values of the transition states can be chosen by known techniques such that between each neighboring $\lambda$ windows on the "reaction pathway" from the reference molecule to the target molecule there is substantial overlap between the micro-states in the successive $\lambda$ windows that are sampled by the molecular simulations.

In performing molecular simulations for all these states, the bonded stretch interaction energy between the two atoms $A_a$ and $A_b$ that are to form a bond (e.g., $A_1$ and $A_3$ in FIG. 1a) can be defined by a soft bond potential which is modulated by $\lambda$ (or the bond stretch component thereof). When $\lambda=0$ ($A_a$ and $A_b$ are completely nonbonded in the reference molecule), the soft bond potential is a flat potential for all distances r between $A_a$ and $A_b$. When $0<\lambda<1$, (the bond between $A_a$ and $A_b$ is being "partially formed" in the alchemical transformation), the soft bond potential levels off to a flat potential when r→∞, i.e., the partial derivative of the potential with respect to the distance r between $A_a$ and $A_b$ is zero when r→∞. When $\lambda=1$ ($A_a$ and $A_b$ are fully valence bonded in the target molecule), the soft bond potential reverts to a harmonic potential. Further, the potential energy function for the bond stretch term does not have any singular regions for all values of the bonded stretch component, $\lambda_{sbs}$, of the coupling parameter $\lambda$ within [0,1] and for all values of the distance r between $A_a$ and $A_b$. The details of developing the soft bond potential and some properties of the soft bond potential are provided below.

During the course of the alchemical transformation from the reference molecule to the target molecule, the interactions unique in the reference molecule can be turned off according to a first set of schedules for different X components, and the interactions unique in the target molecule can be turned on according to a second set of schedules for different $\lambda$ components, as will be further described below.

In commonly-used molecular mechanics force fields, the bonded angle and bonded dihedral angle interactions usually have the following potential energy form:

$$U_{ba}(\theta) = k_\theta(\theta - \theta_0)^2 \qquad (7)$$

$$U_{bd}(\phi) = k_\phi \sum_n f(\cos(n\phi))$$

where $\theta$ is the bond angle, $\theta_0$ is the equilibrium bond angle, $k_\theta$ is the angle force constant (both $\theta_0$ and $k_\theta$ depend on the atoms forming the bond angle); $\phi$ is the dihedral angle, $k_\phi$ is the dihedral angle force constant (which depends on the atoms forming the dihedrals). With the opening or closing of a ring, the bonded angle and dihedral angle terms that are affected by the breaking or forming of the bond can be modulated by components $\lambda_{ba}$ and $\lambda_{bd}$ of the coupling parameter $\lambda$, respectively.

The methods for free energy difference calculations described herein can be applied to a number of highly useful applications, which include, for example:

Relative protein-ligand binding affinity and/or relative solvation free energy calculations between congeneric ligands with ring opening or closing;

Relative protein-ligand binding affinity and/or relative solvation free energy calculations between congeneric ligands that differ by a macrocyclization;

The calculation of the effect of a non-proline to proline or proline to non-proline residue mutation to protein thermodynamic stability, protein-ligand binding affinity, or protein-protein binding affinity; and The calculation of the effect of a residue insertion or residue deletion to protein thermodynamic stability, protein-ligand binding affinity, or protein-protein binding affinity.

Embodiments of the method for the free energy calculations of the disclosed subject matter can be implemented in a computer program, which can take the form of a software component of a suitable hardware platform, for example, a standalone computer, one or more networked computers, network server computers, a handheld device, or the like. Different aspects of the disclosed methods may be implemented in different software modules and executed by one processor or different processors, sequentially or in parallel, depending on how the software is designed. The apparatus on which the program can be executed can include one or more processors, one or more memory devices (such as ROM, RAM, flash memory, hard drive, optical drive, etc.), input/output devices, network interfaces, and other peripheral devices. A computer readable non-transitory media storing the program is also provided.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively, or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a sub combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method, comprising:
   screening a plurality of candidate compounds each being a derivative of a lead compound in a drug lead optimization study, the screening comprising, for each of the plurality of candidate compounds as a target molecule, computing a free energy difference between a reference molecule and the target molecule, the computing comprising:
   providing relative spatial arrangements of atoms and bonded connections between atoms in (i) the reference molecule, the reference molecule comprising a common set of atoms PAB and a set of atoms PA, and
   (ii) the target molecule, the target molecule comprising the common set of atoms PAB and a set of atoms PB;
   defining an initial state, the initial state being a nonphysical molecule composed of the reference molecule and at least one additional atomic component from the set of atoms PB;
   defining a target state, the target state being a nonphysical molecule composed of the target molecule and at least one additional atomic component from the set of atoms PA;
   applying a potential to restrain an interaction of the additional atomic component from the set of atoms PB with the common set of atoms PAB in the initial state;
   applying a potential to restrain an interaction of the additional atomic component from the set of atoms PA with the common set of atoms PAB in the target state;
   determining one or more transition states along a transformation path between the initial state and target state;
   scaling the restrain potential correspondingly along the transformation path until the potential becomes zero when a corresponding end state is reached;
   turning on remaining covalent bonded interactions between the at least one additional atomic component in PB with the common set of atoms PAB and non-bonded interactions along the transformation path until the target state is reached;
   turning on remaining covalent bonded interactions between the at least one additional atomic component in PA with the common set of atoms PAB and the non-bonded interactions along a reverse direction of the transformation path until the initial state is reached; and
   calculating the free energy difference between the reference molecule and the target molecule using a value obtained along the transformation path from the initial state to the target state,
   wherein applying the potential increases the accuracy of the free energy difference calculated while maintaining a configurational space overlap of the initial state and the target state relative to calculating the free energy difference without applying the potential;
   synthesizing one of the candidate compounds based on the calculated free energy differences; and
   lab testing the synthesized candidate compound for the drug lead optimization study.

2. The method of claim 1, wherein the value comprises an energy difference, a derivative of the energy difference, or quantities related to the energy difference.

3. The method of claim 1, wherein the at least one additional atomic component from the set of atoms PB in the initial state comprises the set of atoms PB and the at least one additional atomic component from the set of atoms PA in the target state comprises the set of atoms PA.

4. The method of claim 3, wherein applying the potential and using only one bond angle interaction increases an accuracy of the free energy difference calculation relative to calculating the free energy difference without applying the potential while preventing the additional atomic component from the set of atoms PB or PA from orienting in nonphysical geometry.

5. The method of claim 3, wherein the atom in PAB bonded to the additional atomic component from the set of atoms PB in the target molecule is in a sp3 hybridization, and an equilibrium angle of the potential is set at 120°, and wherein the atom in PAB bonded to the additional atomic component from the set of atoms PA in the initial molecule is in a sp3 hybridization, and an equilibrium angle of the potential is set at 120°.

6. The method of claim 3, wherein an interaction of the at least one additional atomic component from the set of atoms PB in the target molecule and the atoms in PAB is the same when the reference molecule is in a complex form and when the reference molecule is in a solvent.

7. The method of claim 3, wherein an interaction of the at least one additional atomic component from the set of atoms PA in the initial molecule and the atoms in PAB is the same when the target state is in a complex form and when the target state in in a solvent.

8. The method of claim 1, wherein for the additional atomic component from the set of atoms PB bonded to an atom in PAB in the target molecule, the potential is a harmonic potential for a dihedral angle defined by a plane containing three atoms in PAB and a plane containing two atoms in PAB and the additional atomic component from the set of atoms PB.

9. The method of claim 8, wherein the atom in PAB bonded to the atom in PB in the target molecule is in a sp2 hybridization, and an equilibrium angle of the potential is set at 180°.

10. The method of claim 8, wherein determining the one or more transition states along the transformation path comprises calculating a bond stretch interaction between the atom in PAB and the additional atomic component from the set of atoms PB, and one bond angle interaction.

11. The method of claim 1, wherein for the additional atomic component from the set of atoms PA bonded to an atom in PAB in the reference molecule, the potential is a harmonic potential for a dihedral angle defined by a plane containing three atoms in PAB and a plane containing two atoms in PAB and the additional atomic component from the set of atoms PA.

12. The method of claim 11, wherein the atom in PAB bonded to the atom in PA in the initial molecule is in a sp2 hybridization, and an equilibrium angle of the potential is set at 180°.

13. The method of claim 11, wherein determining the one or more transition states along the transformation path comprises calculating a bond stretch interaction between the atom in PAB and the additional atomic component from the set of atoms PA, and one bond angle interaction.

14. The method of claim 1, wherein applying a potential to restrain an interaction of the additional atomic component from the set of atoms PB comprises restraining a set of interactions of the additional atomic component from the set of atoms PB with the common set of atoms PAB in the initial state, and wherein applying a potential to restrain an interaction of the additional atomic component from the set of atoms PA comprises restraining a set of interactions of the additional atomic component from the set of atoms PA with the common set of atoms PAB in the target state.

15. The method of claim 1, wherein the reference molecule is the lead compound.

* * * * *